United States Patent [19]

Hagiwara et al.

[11] Patent Number: 4,525,410
[45] Date of Patent: Jun. 25, 1985

[54] PARTICLE-PACKED FIBER ARTICLE HAVING ANTIBACTERIAL PROPERTY

[75] Inventors: Zenji Hagiwara, Kusatsu; Hideo Ohki, Koshigaya; Shigetaka Hoshino, Sohka; Saburo Nohara, Nishinomiya; Shunya Ida, Nara; Kenichi Tagawa, Osaka, all of Japan

[73] Assignees: Kanebo, Ltd.; Kanto Chemical Co., Inc., both of Tokyo, Japan

[21] Appl. No.: 525,980

[22] Filed: Aug. 24, 1983

[30] Foreign Application Priority Data

Aug. 24, 1982 [JP] Japan ................................ 57-145549

[51] Int. Cl.$^3$ ...................... A61K 9/70; A61K 33/34; A61K 33/38; D06M 11/04
[52] U.S. Cl. ........................................ 428/198; 5/482; 5/490; 5/495; 5/DIG. 1; 424/23; 424/27; 424/131; 424/132; 424/140; 424/145; 424/157; 428/241; 428/283; 428/296; 604/360; 604/367
[58] Field of Search ..................... 424/23, 27, DIG. 7, 424/79, 132, 140, 145, 157, 357; 604/359, 360, 367; 428/283, 296, 241, 198

[56] References Cited

U.S. PATENT DOCUMENTS 2,813,056 11/1957 Davis et al. ......................... 424/132
2,850,405 9/1958 Bottoms ............................... 424/140
2,856,330 10/1958 Vagenius ............................. 424/140
3,016,327 1/1962 Schmitz et al. ....................... 424/79
3,542,504 11/1970 Schofield et al. .................... 424/132
3,922,723 12/1975 Popper ................................ 604/359
3,959,556 5/1976 Morrison .
3,971,373 7/1976 Braun ................................ 128/146.2
4,231,118 11/1980 Nakagawa ............................. 2/7
4,343,853 8/1982 Morrison .
4,401,712 8/1983 Morrison .
4,433,024 2/1984 Eian ................................... 428/198

FOREIGN PATENT DOCUMENTS 38358 3/1980 Japan .

Primary Examiner—James C. Cannon
Attorney, Agent, or Firm—Cushman, Darby & Cushman

[57] ABSTRACT

Specific zeolite particles retaining therein a metal ion having a bactericidal activity are packed and retained in a mixed fiber assembly composed of low-melting thermoplastic synthetic fibers and ordinary fibers. The zeolite particles are retained by welding of the low-temperature thermoplastic synthetic fibers but in a state of allowing the contact thereof with an external fluid. The particle-packed fiber article has an excellent and durable antibacterial activity and can be used in various fields.

4 Claims, 3 Drawing Figures

PARTICLE-PACKED FIBER ARTICLE HAVING ANTIBACTERIAL PROPERTY

FIELD OF THE INVENTION

This invention relates to a fiber article having an antibacterial property containing therein zeolitic solid particles having an antibacterial activity. More particularly, the invention relates to a fiber article having an antibacterial property, which retains zeolitic particles having a bactericidal activity in fibers having fused intersection points and capable of contacting with external fluids through the cavities in the fibers.

BACKGROUND OF THE INVENTION

It is known for a long time that a silver ion, a copper ion and a zinc ion have an antibacterial property. For example, a silver ion is widely utilized as a disinfectant or a germicide in the form of a solution of silver nitrate. However, the user of silver nitrate as a form of solution is inconvenient for handling as well as there is a fault that such a form is used for only restricted purposes.

Furthermore, it is attempted to adsorb a silver ion on an adsorbent such as activated carbon, alumina, silica gel, etc., and pack the adsorbent in a vessel or fix the adsorbent with a resin for bactericidal use. However, such a utilization has faults that the application of the bactericidal material is restricted and also the exchange operation of the bactericidal material is troublesome. In particular, the foregoing method of fixing the silver-adsorbed material with a resin encounters a difficulty that the property of the adsorbent is sacrificed and hence it is difficult to utilize such a method in various fields.

On the other hand, Japanese Patent Publication (Unexamined) No. 38,358/1980 discloses a bactericidal material mainly composed of a high molecular material having a functional group in the form of a complex with a silver ion, a copper ion or a zinc ion. However, the bactericidal material is a film-shaped material and hence such a material is used only for restricted purposes.

SUMMARY OF THE INVENTION

Therefore, as the result of various investigations for overcoming the foregoing difficulties, the inventors have discovered that a fiber article having an antibacterial property, which has various merits in the points of antibacterial activity, durability of effect, etc., and can be effectively and widely utilized, is obtained by fixing an antibacterial metal ion onto a zeolite material having a specific property for stabilization and surely incorporating the metal ion-fixed zeolite material in a fiber article which can be easily fabricated into a desired form, and based on the discovery, the present invention has been attained.

That is, according to the present invention, there is provided a particle-packed fiber article having an antibacterial property comprising zeolitic particles retaining therein at least one metal ion having a bactericidal property and having a specific surface area of at least 150 m$^2$/g and a SiO$_2$/Al$_2$O$_3$ mol ratio of at most 14 and a mixed fiber assembly composed of a natural fiber staple or synthetic fiber staple and a fiber staple containing low-melting thermoplastic synthetic fibers having a melting point at least 30° C. lower than the melting point or the decomposition point of the aforesaid natural fiber staple or synthetic fiber staple, at least a part of the intersection points of the staple of said mixed fiber assembly being stuck to each other by the fusion of the low-melting thermoplastic synthetic fibers, whereby said zeolitic particles are incorporated and retained in the fiber assembly in the state of allowing the contact of the foregoing zeolitic particles with an external fluid.

DESCRIPTION OF THE PREFERRED EMBODIMENT

The zeolitic solid particles having a bactericidal activity in this invention are natural or synthetic zeolite particles retaining one or more metal ions having a bactericidal activity at the ion-exchangeable sites thereof. Preferred examples of metal ions having a bactericidal activity are ions of Ag, Cu, Zn. Therefore, these metals can be used solely or as a mixture of them for the foregoing purpose of this invention.

Zeolite is generally aluminosilicate having a three-dimensionally grown skeleton structure and is generally shown by $xM_{2/n}O \cdot Al_2O_3 \cdot ySiO_2 \cdot zH_2O$ with Al$_2$O$_3$ as a standard, wherein M represents an ion-exchangeable metal ion, which is usually the ion of a monovalent or divalent metal; n corresponds to the valence of the metal; x is a coefficient of the metal oxide; y is a coefficient of silica; and z is a number of water of crystallization. Various kinds of zeolites having different component ratios, fine pore diameters, and specific surface areas are known.

However, it is required that the specific surface area of the zeolitic solid particles used in this invention is at least 150 m$^2$/g (anhydrous zeolite as standard) and the SiO$_2$/Al$_2$O$_3$ mol ratio as the zeolite constituting components is at most 14, preferably at most 11.

Since a solution of a water-soluble salt of a metal having a bactericidal activity used in this invention, such as silver, copper, and zinc easily causes an ion exchange with zeolite defined in this invention, the foregoing metal ions can be retained on the solid phase of zeolite solely or as a mixture of them by utilizing such an ion exchange phenomenon but in this case the zeolitic particles retaining the metal ion or ions must satisfy the conditions that the specific area is at least 150 m$^2$/g and the SiO$_2$Al$_2$O$_3$ mol ratio is at most 14. It has been found that, if the zeolitic particles do not satisfy the foregoing conditions, a desired product having an effective bactericidal activity cannot be obtained. This is considered to be based on that the absolute amount of the metal ion or ions fixed to zeolite in the state of exhibiting the effect. In other words, it is considered to be based on the physicochemical properties such as the amount of the exchange group of zeolite, the exchange rate, the accessibility, etc.

Therefore, a zeolite having a larger SiO$_2$/Al$_2$O$_3$ ratio, which is known as a molecular sieve is utterly unsuitable in the invention of this application.

Also, it has been found that zeolite having a SiO$_2$/Al$_2$O$_3$ mol ratio of at most 14 can uniformly retain the metal ion having a bactericidal activity, whereby a sufficient bactericidal activity can be obtained by using such a zeolite. In addition, the acid resistance and alkali resistance of zeolite having a high $SiO_2/Al_2O_3$ mol ratio over 14 become larger with the increase of the content of $SiO_2$ but, on the other hand, it takes a long period of time to prepare such a zeolite and hence the use of the zeolite having such a high silica content is not profitable from economical aspect. The natural or synthetic zeolite having a $SiO_2/Al_2O_3$ of at most 14 can be sufficiently used from the point of acid resistance and alkali resistance in an ordinary utilization field of the article as well as is inexpensive from economical aspect and, therefore, can be advantageously used. From these view points, it is required that the $SiO_2/Al_2O_3$ mol ratio of the zeolitic particles be at most 14.

As the zeolite material having a $SiO_2/Al_2O_3$ mol ratio of at most 14 used in this invention, any natural or synthetic zeolites can be used. Examples of natural zeolite used in this invention are analcime ($SiO_2/Al_2O_3 = 3.6$ to 5.6), chabazite ($SiO_2/Al_2O_3 = 3.2$ to 6.0 and 6.4 to 7.6), clinoptilolite ($SiO_2/Al_2O_3 = 8.5$ to 10.5), erionite ($SiO_2/Al_2O_3 = 5.8$ to 7.4), faujasite ($SiO_2/Al_2O_3 = 4.2$ to 4.6), mordenite ($SiO_2/Al_2O_3 = 8.34$ to 10.0), phillipsite ($SiO_2/Al_2O_3 = 2.6$ to 4.4). These typical natural zeolites can be preferably used in this invention. On the other hand, typical examples of synthetic zeolites used in this invention are A-type zeolite ($SiO_2/Al_2O_3 = 1.4$ to 2.4), X-type zeolite ($SiO_2/Al_2O_3 = 2$ to 3), Y-type zeolite ($SiO_2/Al_2O_3 = 3$ to 6), mordenite ($SiO_2/Al_2O_3 = 9$ to 10). Particularly preferred examples of the zeolite used in this invention are synthetic A-type zeolite and X-type zeolite, and natural mordenite.

The suitable form of zeolite used in this invention may be fine particles or the assembly of the fine particles. As the form of the assembly, there are, for example, pellets, granules. In the case of using the zeolite as the form of powder, however, it is preferred that the particle size of the powder be larger than 1 micron for retaining the zeolite powder stably in the fiber assembly.

The metal-zeolite having a bactericidal activity used in this invention can be prepared by utilizing the ion exchange reaction as described above. For example, in the case of preparing the Ag-zeolite of this invention using various kinds of zeolites as defined in this invention, an aqueous solution of a water-soluble silver salt such as silver nitrate is usually used at the conversion to the Ag-zeolite and in this case it must be noticed that the concentration of the solution does not become too high. For example, if the silver ion concentration is too high, e.g., 1 to 2M (molarity; hereinafter the same) $AgNO_3$, in the case of converting an A-type zeolite or an X-type zeolite (i.e., sodium-type zeolite) into an Ag-zeolite by utilizing an ion-exchange reaction, the silver ion in the solution forms silver oxide in the solid phase of the zeolite as the percipitates simultaneously when the silver ion is replaced with the sodium ion of the solid phase of the zeolite. The precipitation of the silver oxide on the zeolite reduces the porosity of the zeolite, whereby the specific surface area of the zeolite is greatly reduced. Also, even when the reduction of the specific surface area of the zeolite is not so serious, the bactericidal activity of the Ag-zeolite is reduced by the presence of the silver oxide itself. For preventing the deposition of such excessive silver onto the solid phase of zeolite, it is necessary to maintain the concentration of the silver solution at a diluted state, e.g., lower than 0.3M $AgNO_3$, preferably lower than 0.1M $AgNO_3$ (as shown in Example 1). It has been found that in the case of using an aqueous $AgNO_3$ solution of such a concentration, the specific surface area of the Ag-zeolite thus obtained is almost same as that of the original zeolite and the effect of the bactericidal activity can be utilized at the optimum condition.

In the case of converting the zeolite defined in this invention into a Cu-zeolite, the same phenomenon as mentioned above for an Ag-zeolite will take place according to the concentration of a solution of a copper salt used for the ion-exchange reaction. For example, when an aqueous solution of 1M $CuSO_4$ is used in the case of converting an A-type or an X-type zeolite (sodium-type zeolite) into a Cu-zeolite by an ion-exchange reaction, $Cu^{2+}$ in the solution is replaced with $Na^+$ of the solid phase of the zeolite but at the same time, basic precipitates such as $Cu_3(SO_4)(OH)_4$ deposit in the solid phase of the zeolite, whereby the porosity of the zeolite is reduced and thus the specific surface area thereof is also greatly reduced. For preventing the deposition of the copper ion onto the solid phase of zeolite, it is preferred to maintain the concentration of an aqueous solution of a water-soluble copper salt used in this invention at a diluted state, for example, lower than 0.05M (as shown in Example 1). It has also been found that in the case of using an aqueous $CuSO_4$ solution of such a concentration, the specific surface area of the Cu-zeolite obtained is almost same as that of the original zeolite and the bactericidal effect is obtained at the optimum condition.

As stated above, at the conversion into an Ag-zeolite or Cu-zeolite, there is a deposition of a solid material onto the solid phase of the zeolite according to the concentration of a salt used for the ion-exchange reaction. However, at the conversion into a Zn-zeolite, there occurs no such a phenomenon when the concentration of a solution of a salt used is about 2 to 3M. Usually, the Zn-zeolite to be used in this invention can be easily obtained by using a solution of a zinc salt having the foregoing concentration of 2 to 3M (as shown in Example 1).

When the ion-exchange reaction for the conversion into an Ag-zeolite, a Cu-zeolite or a Zn-zeolite is performed in a batch method, the zeolite may be immersed in the metal salt solution having the foregoing concentration. In order to increase the content of a metal in the zeolite, the batch treatment may be repeated. On the other hand, in the case of treating the foregoing zeolite in a column method using a metal salt solution having the aforesaid concentration, the desired metal-zeolite is easily obtained by packing the zeolite in an adsorption column and passing a solution of the metal salt through the column.

The amount of the metal incorporated in the aforesaid metal-zeolite (the zeolite dried at 100° C. as a standard) may be less than 10% by weight in the case of silver and is preferably 0.001 to 5% by weight. On the other hand, in the case of zinc or copper, the amount of zinc or copper incorporated in the metal-zeolite may be less than 25% by weight and is preferably 0.01 to 15% by weight.

The bonding strength between the zeolite defined in this invention and an antibacterial metal ion such as a zinc ion, a silver ion, and a copper ion is very high different from the case of making retain the metal ion onto an adsorptive material such as activated carbon, alumina, etc., by simply a physical adsorption. Therefore, the strong bactericidal function of the fiber article containing such a metal-zeolite and a long durability of the bactericidal effect are the specific features of this invention.

The zeolite defined in this invention has a merit that the reactivity thereof with a metal having a bactericidal activity, such as Ag, Cu, and Zn is high. For example, the ion-exchangeable metal ion ($Na^+$) is an A-type zeolite, X-type zeolite, a Y-type zeolite, or chabazite easily causes an ion-exchange reaction with $Ag^+$, $Cu^{2+}$, or $Zn^{2+}$ to retain the bactericidal metal ion in the zeolite with a high retaining power. Also, the zeolite defined in this invention has a merit that the selectivity for the adsorption of $Ag^+$, $Cu^{2+}$, or $Zn^{2+}$ is high. Such a fact means that when a fiber article of this invention is used in a liquid or water containing various metal ions for the purpose of pasteurization, $Ag^+$, $Cu^{2+}$, or $Zn^{2+}$ is stably retained in the zeolite for a long period of time as well as the bactericidal activity of the fiber article can be maintained for a long period of time.

In addition, the zeolite defined in this invention also has such merits that the ion-exchange capacity is large and $Ag^+$, $Cu^{2+}$, or $Zn^{2+}$ having a bactericidal activity can be largely retained in the zeolite. Furthermore, the zeolite defined in this invention has a merit that the amount of $Ag^+$, $Cu^{2+}$, or $Zn^{2+}$ contained in the zeolite particles can be easily controlled in an ion exchange in accordance with the purpose of using the fiber article of this invention. The zeolite having a $SiO_2/Al_2O_3$ mol ratio of at most 14 and a specific surface area of at least 150 $m^2/g$ used in this invention has a large ion-exchange capacity, e.g., 5 meq/g for chabazite, 2.6 meq/g for mordenite, 3.8 meq/g for erionite, 2.6 meq/g for clinoptilolite, 7.0 meq/g for A-type zeolite, 6.4 meq/g for X-type zeolite, and 5.0 meq/g for Y-type zeolite (the foregoing numerical values are rough values of the ion-exchange capacity per unit weight of the zeolite (as anhydrous zeolite)).

Examples of the material for the low-melting thermoplastic synthetic fibers used in this invention are polyvinyl chloride, polyvinylidene chloride, polyethylene, polypropylene, an ethylene-propylene copolymer, an ethylenevinyl acetate copolymer, polystyrene, nylon 6, nylon 66, nylon 610, copolymerized polyamides, polyethylene terephthalate, polybutylene terephthalate, polyethylene isophthalate, polyhexamethylene terephthalate, copolymerized polyesters.

The fiber staple containing the low-melting thermoplastic synthetic fibers used in this invention may be composed of the low-melting thermoplastic synthetic fibers only. Also, the fiber staple may be a staple composed of a high-melting component having a relatively high melting point coated partially or wholly with the foregoing low-melting component or may be a staple of sheath-one type composite fibers composed of a high-melting component as the core material and the low-melting component formed thereon as a sheath or conjugate type composite fibers composed of both components. For example, there are composite fibers composed of polyethylene terephthalate as the high-melting component and polypropylene, polystyrene, polyamide, or copolymerized polyester as the low-melting component and composite fibers composed of polypropylene as the high-melting component and polyethylene, an ethylene-propylene copolymer, or an ethylene-vinyl acetate copolymer as the low-melting component.

Any other natural fiber staples and synthetic fiber staples may be also used in the mixed fiber assembly according to this invention. However, when synthetic fiber staple is selected, it is preferred to use synthetic fibers of the same system as the low-melting thermoplastic synthetic fibers. Also, in the case of using composite fibers, it is preferred that the high-melting component is also a polymer of the same system. In these cases, it is particularly preferred that the synthetic fiber staples and the low-melting thermoplastic synthetic fibers (and the high-melting component) are all composed of polyester series polymers.

The fiber length of the foregoing fibers may be 30 to 100 mm, which is an ordinary staple length, and further the fineness or size of the fibers may be usually 1 to 20 deniers.

The mixed fiber assembly in this invention means a web such as a parallel web, a cross web, a random web and the like, prepared by mixing the foregoing natural fiber staple or synthetic fiber staple and a fiber staple containing the low-melting thermoplastic synthetic fibers having a melting point at least 30° C. lower than the melting point or the decomposition point of the aforesaid staple at a proper ratio and fabricating the mixture by means of a proper weaving machine or a needle punching non-woven fabric of the said web.

One of the features of the mixed fiber assembly is that by performing a heat treatment at a temperature condition of higher than the melting point of the low-melting thermoplastic synthetic fibers and lower than the melting point or the decomposition point of the natural fiber staple or the (high-melting) synthetic fiber staple, the low-melting synthetic fibers are almost melted to stick the plural staples to each other at the intersection points, whereby zeolite particles are retained in the fiber assembly in a state incorporated therein. Other feature of the mixed fiber assembly is that since sticking occurs at the staple intersection points only, less formation of film can be observed compared with the case of adhesion by impregnation of a binder, which prevents the reduction of porosity of the fiber assembly and the reduction in the function of the zeolite solid particles. Still other feature of the mixed fiber assembly is that by pressing the low-melting synthetic fibers while they are in a molten state after heating or by simultaneous heating and pressing the low-melting synthetic fibers, the bulkiness, the elasticity, and pore size of the fiber assembly can be controlled and the fiber assembly can be stuck in a body.

Hitherto, there is known a particles-containing sheet prepared by dispersing activated carbon, alumina particles and the like in a fiber assembly for, for example, removing noxious gases in air. However, in such a sheet, it is difficult to uniformly incorporate the solid particles in a fluffy fiber assembly. As a still larger faults of the aforesaid sheet, there frequently occurs a phenomenon that the solid particles in the completed sheet move through the cavities of the fiber assembly as the result of handling or vibrating the sheet or as the result of the action of air stream passing through the sheet and in an estreme case the particles flow out of the sheet, whereby there form portions having a low density of the particles to cause the passage of noxious gases at the low-density portions and to shorten the effective life of the sheet. Also, even when the proportion of particles contained in the sheet is increased, it increases pressure loss in vain and it is frequently difficult to sufficiently exhibit the function of the particles.

On the other hand, in the case of using the mixed fiber assembly of this invention, the mixed fiber assembly firmly retain therein zeolitic solid particles to such an extent that the influence by the vibration at operation or by flowing of an external medium is very small, and also the pressure loss by the passage of an external fluid can be restricted in a practical range.

The mixing ratio of the natural fiber or synthetic fiber staple to the staple containing the low-melting thermoplastic composite fibers in the mixed fiber assembly of this invention is preferably from 90:10 to 10:90 by weight ratio. In this case, if the proportion of the natural fiber or synthetic fiber staple is over 90%, the density of heat welded points among the fibers of the fiber article becomes too small and sticking of fibers in the body is insufficient, whereby fibers are liable to separate. On the other hand, if the proportion of the natural fiber or synthetic fiber staple is less than 10%, the welded components becomes too large, the fiber article thus obtained is lacking in flexibility, and the contact of the zeolitic solid particles contained in the article with an external fluid is reduced.

Furthermore, the density of the mixed fiber assembly in this invention is preferably 0.05 to 0.5 g/cm$^3$. If the density of the mixed fiber assembly is less than 0.05 g/cm$^3$, depending upon the diameter or size of zeolitic solid particles or the assemblies thereof packed or contained in the mixed fiber assembly, the movement of the packed material occurs by the vibration of the fiber article at the operation thereof or by the flow of an external medium, which results in the reduction of the contact of the packed material with an external fluid and the reduction in the function of the packed material. On the other hand, if the density of the mixed fiber assembly is higher than 0.5 g/cm$^3$, the pressure loss at the passage of an external fluid becomes larger to cause a trouble in case of practical use.

The density of the mixed fiber assembly can be controlled by property controlling the pressure at the heat treatment for sticking plural staples at the intersection points of the staples by melting the low-melting thermoplastic synthetic fibers to unite the fiber assembly and solid particles in a body.

As a method for uniting the mixed fiber assembly and zeolitic solid particles in a body, there are a method of heating the mixed fiber assembly, applying thereto zeolitic solid particles or assemblies thereof to contact with the mixed fiber assembly while the low-melting thermoplastic synthetic fibers are in a molten state, applying pressure to the mixed fiber assembly, then cooling it to fix the particles onto the mixed fiber assembly and a method of subjecting the mixed fiber assembly solely to a pre-heating and pre-pressing treatment to form a sheet having controlled bulkiness, elasticity, and pore size, packing zeolitic solid particles in the sheet, and then heating and pressing the sheet again to fix the particles onto the fiber assembly in a body. In the case of employing the latter method, it is preferred from the point of firmly fixing the zeolitic solid particles onto the fiber assembly in a body to perform the last heating and pressing treatment at higher temperature and pressure for longer period of time than those in the pre-heating and pressing treatment.

It is proper that the proportion of the zeolitic solid particles having a bactericidal effect in the fiber article is in a range of 0.1 to 60% by weight. If the proportion is less than 0.1% by weight, the bactericidal effect to an external fluid is insufficient. On the other hand, if the proportion is over 60% by weight, the bactericidal effect cannot increase any more. The most preferred proportion of the metal-zeolite having a bactericidal effect according to this invention is 0.5 to 45% by weight to the amount of fibers.

When the mixed fiber assembly is composed of a natural fiber or synthetic fiber staple and a staple of thermoplastic synthetic fibers alone having a melting point at least 30° C. lower than the melting point or the decomposition point of the foregoing staple, the heating temperature of the mixed fiber assembly is between the melting point or the decomposition point of the natural fibers or synthetic fibers and the melting point of the low-melting thermoplastic synthetic fibers. Also, when the mixed fiber assembly is composed of a natural fiber or synthetic fiber staple and a thermoplastic composite fiber staple composed of a high-melting component wholly or partially coated with a low-melting component having a melting point at least 30° C. lower than the melting point or the decomposition point of the foregoing staple, the difference between the melting point of said low-melting component and the melting point of said high-melting component being larger than 30° C., the heating temperature for the mixed fiber assembly is established in a range of from the lower temperature between the melting point or the decomposition point of the natural fibers or synthetic fibers and the melting point of the high-melting component of the thermoplastic composite fibers to the melting point of the low-melting component of the thermoplastic composite fibers. Also, when the mixed fiber assembly is composed of foregoing three kinds of staples, the heating temperature for the mixed fiber assembly is established in a range of from the lower temperature between the melting point or the decomposition point of the natural fibers or synthetic fibers and the melting point of the high-melting component of the thermoplastic composite fibers to the higher temperature between the melting point of the low-melting thermoplastic synthetic fibers and the melting point of the low-melting component of the thermoplastic composite fibers.

As a heating method, dry heating such as indirect heating by hot blast, infrared heater, and direct heating by a heating plate, a heating roll, or wet heating by hot water, steam, high-pressure steam, may be employed. As a pressing means, a press system, a roll system and the like may be properly employed.

The fiber article of this invention retaining therein zeolitic solid particles having a bactericidal effect has a merit of effectively utilizing the bactericidal effect of the metal-zeolitic solid particles in various utilization fields as compared to the foregoing known method such as a method of using a solution of a bactericidal metal or a method of utilizing a bactericidal metal by applying it onto an adsorbent by a simple physical adsorption and then packing the adsorbent in a vessel or fixing the adsorbent with a resin. In addition, the fiber article of this invention is excellent in a point that the article can be easily equipped to a desired place and a point of workability.

In other words, the fiber article of this invention contains zeolitic solid particles without reducing the bactericidal effect of the metal-zeolitic solid particles and since the fiber article can be fabricated into a sheet, a tape as well as can be molded into blocks, hollow blocks (e.g. hollow cylinders), of any desired forms, the fiber article can be utilized in various fields. Moreover, as described above, the fiber article of this invention can be very easily equipped to a desired place or can be very easily replaced and also since a bactericidal metal is retained on the active zeolite, the article of this invention is excellent in bactericidal function and the long durability.

Practically, mats, beds, bedclothes, pillows and the like, having the fiber article of this invention as the outside cover layer and also filters, insoles of shoes, general sanitary goods, obtained by molding or laminating the article are suitable applications of the fiber article of this invention.

Then, the invention will be further explained by the following examples but the invention is not limited to these examples so far as the invention is not over the scope of this invention.

EXAMPLE 1

To 250 g of each of the fine dry powder of 6 kinds of the natural and synthetic zeolites described in Table 1 was added 500 ml of an aqueous 1/10M silver nitrate solution and the mixture thus obtained was stirred for 3 hours at room temperature to perform the ion exchange. After filtering the silver-zeolite obtained by such an ion-exchange method, the silver-zeolite was washed with water to remove excessive silver ion. Then, the silver-zeolite thus washed was dried at 100° to 105° C. and then crushed to provide fine powder of the silver-zeolite. The silver content and the specific surface area of the silver-zeolite thus obtained are shown in Table 1.

TABLE 1

| Used zeolite | Silver content (%) of silver-zeolite | Specific surface area ($m^2/g$) of silver-zeolite |
|---|---|---|
| A-type zeolite ($0.94Na_2O.Al_2O_3.1.92SiO_2.xH_2O$: fine powder finer than 100 mesh) | 2.1 | 629 |
| X-type zeolite ($0.99Na_2O.Al_2O_3.2.55SiO_2.xH_2O$: fine powder finer than 100 mesh) | 2.1 | 831 |
| Y-type zeolite ($1.14Na_2O.Al_2O_3.4.90SiO_2.xH_2O$: fine powder finer than 200 mesh) | 2.1 | 875 |
| Natural mordenite (made by Shin Tohoku Kagaku Kogyo K. K.; $SiO_2/Al_2O_3 = 9.8$: fine powder finer than 100 mesh) | 1.13 | 329 |
| Natural mordenite (2020A, trade name, made by Anaconda Minerals Company: fine powder finer than 100 mesh) | 0.23 | 174 |
| Natural chabazite (5050L, trade name, made by Anaconda Minerals Company: fine powder finer than 100 mesh) | 0.17 | 474 |

(Hereinafter, in the converted silver-zeolites described above, the silver-A type zeolite is abbreviated as $Z_1$, the silver-X type zeolite as $Z_2$, the silver-Y type zeolite as $Z_3$, the silver-natural mordenite (made by Shin Tohoku Kogaku Kogyo K. K.) as $Z_4$, the silver-natural mordenite (made by Anadonda Minerals Company) as $Z_5$, and the silver-natural chabazite as $Z_6$.)

Each of the converted silver-zeolites $Z_1$ to $Z_6$ obtained by the foregoing method was packed in the fiber assembly and they were united in a body by the following manner to provide test pieces of the particle-packed fiber articles of this invention.

A polyethylene terephthalate staple (melting point 260° C.) having a size of 6 deniers and a fiber length of 51 mm was mixed with a copolymerized polyester staple (melting point 110° C.) of terephthalic acid and isophthalic acid of a copolymerization ratio of 60:40 (by mol ratio) having a size of 6 deniers and a fiber length of 51 mm at a mixing ratio of 70:30 by weight and a web was formed from the mixture by means of a random weaving machine and laminated to provide a web having a weight of 200 g/m². The web was pre-heated and pre-pressed by means of a pair of stainless steel rolls having a roll surface temperature of 110° C. and a line pressure of 20 kg/cm to form a sheet. Since the foregoing heating and pressing were performed for a short period of time, the surface of the sheet was in a state of web having small fluffs. The foregoing silver-zeolite powder was spread over the sheet thus obtained by a vibration method, the same kind of sheet was placed on the aforesaid sheet and they were heated and pressed again for one minute by means of a bed press machine at a temperature of 130° C. a pressure of 10 kg/cm², whereby the sheets and the silver-zeolite powder were united in a body by melt sticking of low-melting polyester.

The fiber density in the test piece was 0.2 g/cm³ and the proportion of the silver-zeolite powders $Z_1$ to $Z_6$ each was about 25% (as anhydrous zeolite) to the fibers.

The evaluation of the bactericidal activity of the foregoing 6 kinds of the silver-zeolite powder-packed fiber articles and tests for the extinction rate of Eumycetes and for the durability of the bactericidal activity were performed by the following test methods.

(1) Test method for the evaluation of bactericidal activity:

A bactericidal activity test by a disc method was performed. Each of the aforesaid 6 kinds of the silver-zeolite powder-packed fiber articles was cut into a disc of 8 mm in diameter to provide a test disc. A Mueller Hinton culture medium was used for bacteria and a Sabourand medium was used for Eumycetes. Test bacteria or fungi were floated on a physiological saline solution at $10^8$/ml and then was dispersed in the culture medium by means of a Conradi rod at 0.1 ml. Then, the test disc was placed on the medium.

The bactericidal activity was evaluated by observing the presence of an inhibition zone formation after cultivating for 18 hours at 37° C. in the case of bacteria and by observing the presence of an inhibition zone formation after cultivating for one week at 30° C. in the case of Eumycetes.

(2) Method of measurement for the extinction rate of Eymycetes:

Each of the 6 kinds of the silver-zeolite powder-packed fiber articles of this invention was immersed in a suspension of the spores ($10^4$ spores/ml) of *Aspergillus flavus* for 24 hours at 30° C. Then, the suspension was sampled, diluted, and the diluted sample was dispersed in a Sabourand ager medium and then maintained for 24 hours at 30° C. Thereafter, the number of living spores was measured and the extinction rate was calculated.

(3) Test method for the durability of bactericidal activity:

Each of the 6 kinds of the test pieces of the fiber articles of this invention was immersed in still water or running water, whereby the relation between the bactericidal activity and the passage of time was obtained. The aforesaid test was performed by a disc method until the bactericidal activity was vanished. At these tests, *Candida albicans* was used as the test bacteria. At the still water test, water was exchanged every 15 hours.

The evaluation results of the bactericidal activity are shown in Table 2, the measurement results for the extinction rate of Eumycetes are shown in Table 3, and the evaluation results for the durability of bactericidal activity are shown in Table 4. The sample marks of the silver-zeolite powder-packed fiber articles shown in Tables 2 to 4 are as follows:

$F_1$: Fiber article packed with silver-A type zeolite powder ($Z_1$).
$F_2$: Fiber article packed with silver-X type zeolite powder ($Z_2$).
$F_3$: Fiber article packed with silver-Y type zeolite powder ($Z_3$).
$F_4$: Fiber article packed with silver-natural mordenite powder ($Z_4$).
$F_5$: Fiber article packed with silver-natural mordenite powder ($Z_5$).
$F_6$: Fiber article packed with silver-natural chabazite powder ($Z_6$).

TABLE 2

(Evaluation of bactericidal activity)

| Kind of test fungus | $F_1$ | $F_2$ | $F_3$ | $F_4$ | $F_5$ | $F_6$ |
|---|---|---|---|---|---|---|
| *Escherichia coli* | + | + | + | + | − | − |
| *Pseudomonas aeruginosa* | + | + | + | + | + | + |
| *Staphylococcus aureus* | + | + | − | + | + | + |
| *Candida albicans* | + | + | + | + | + | + |

TABLE 3

(Extinction rate of Eumycetes)

| Kind of test fungus | $F_1$ | $F_2$ | $F_3$ | $F_4$ | $F_5$ | $F_6$ |
|---|---|---|---|---|---|---|
| *Aspergillus flavus* | 100% | 100% | 100% | 100% | 99% | 99% |

TABLE 4

(Evaluation of durability of bactericidal activity)

| Test state | $F_1$ | $F_2$ | $F_3$ | $F_4$ | $F_5$ | $F_6$ |
|---|---|---|---|---|---|---|
| Immersed in still water | >16 m.* | >16 m. | >16 m. | >16 m. | >16 m. | >16 m. |
| Immersed in running water | >12 m. | >12 m. | >12 m. | >12 m. | >12 m. | >12 m. |

(m): Month

As is clear from Table 2, it has been confirmed that the silver-zeolite powder-packed fiber articles $F_1$, $F_2$ and $F_4$ are excellent in antibacterial property to the test fungi. It has also been confirmed that the silver-zeolite powder-packed fiber article $F_3$ is excellent in antibacterial property to the three kinds of test fungi *Staphylococcus aureus* and the fiber articles $F_5$ and $F_6$ are excellent in antibacterial property to the three kinds of the test fungi except *Escherichia coli*. Furthermore, as is clear from Table 3, the bactericidal activity to *Aspergillus flavus* is 100% for the fiber articles $F_1$ to $F_4$ and higher than 90% for the fiber articles $F_5$ and $F_6$. Still further, as is clear from Table 4, it has also been confirmed that the silver-zeolite powder-packed fiber articles of this invention maintain the antibacterial activity for a long period of time.

COMPARISON EXAMPLE 1

Each of the dry products of the fine powders of the six kinds of the silver-unconverted natural and synthetic zeolites as used in Example 1 was packed in a fiber assembly by the same manner and packing ratio as in Example 1 to provide a zeolite powder-packed fiber article.

When the evaluation of the antibacterial activity of said fiber articles and the test for the extinction ratio of Eumycetes by the fiber articles were performed by the same methods as in Example 1 using the same test fungi as in Example 1, no inhibition zone was formed and the extinction rate was 0%.

EXAMPLE 2

To 250 g of each of the dry fine powders of 4 kinds of the natural and synthetic zeolites described in Table 5 was added 1 liter of an aqueous 1/20M copper sulfate solution and the resultant mixture was stirred for 5 hours at room temperature to perform an ion-exchange reaction. Then, the copper-zeolite thus obtained by such an ion-exchange method was filtered by suction and washed with water until the sulfate ion disappeared. Thereafter, the washed copper-zeolite of converted copper-zeolite.

Figure 1:
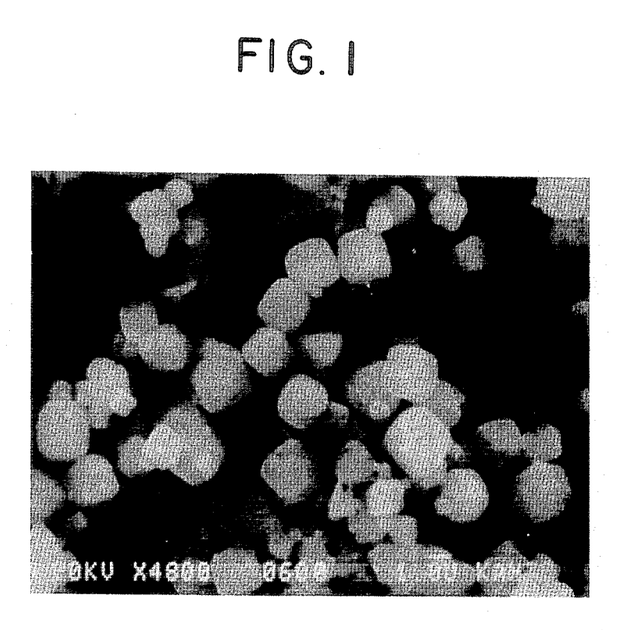
FIG. 1 is an electromicroscopic photograph of an unconverted A-type zeolite powder.
Figure 2:
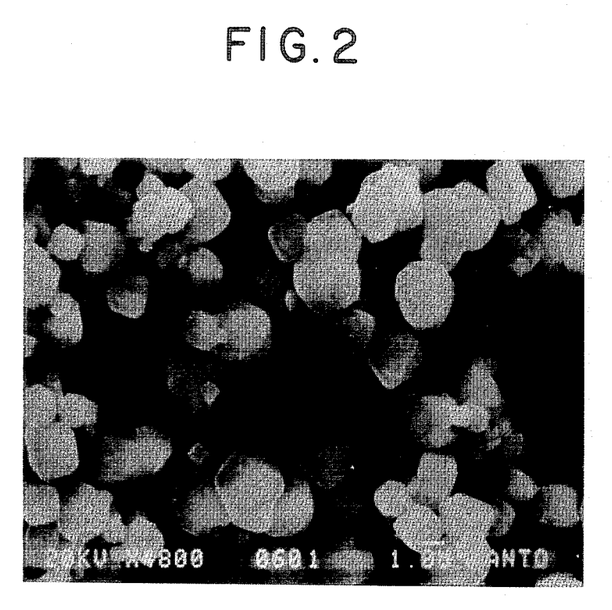
FIG. 2 is an electromicroscopic photograph of a converted copper-A-type zeolite according to this invention (Example 2)

The copper content and the specific surface area of each of the copper-zeolites converted by the foregoing method are shown in Table 5. In addition, the scanning electron microscopic photographs of the unconverted A-type zeolite and the converted copper-A type zeolite are shown in FIG. 1 and FIG. 2, respectively.

TABLE 5

| Zeolite | Copper content (%) of converted copper-zeolite | Specific surface area ($m^2/g$) of converted copper-zeolite |
|---|---|---|
| A-type zeolite* | 1.08 | 649 |
| Y-type zeolite* | 1.21 | 903 |
| Natural mordenite* | 0.29 | 179 |
| Natural chabazite* | 0.10 | 506 |

*A-type zeolite: $0.94Na_2O.Al_2O_3.1.92SiO_2.xH_2O$: fine powder finer than 100 mesh.
Y-type zeolite: $1.14Na_2O.Al_2O_3.4.90SiO_2.xH_2O$: fine powder finer than 200 mesh.
Natural mordenite: 2020A, trade name, made by Anaconda Minerals Company, fine powder finer than 100 mesh.
Natural chabazite: 5050L, trade name, made by Anaconda Minerals Company, fine powder finer than 100 mesh.

(In the converted copper-zeolites, the copper-A type zeolite is abbreviated as $Z_7$, the copper-Y type zeolite as $Z_8$, the copper-natural mordenite as $Z_9$ and copper-natural chabazite as $Z_{10}$.)

Each of the copper-zeolites $Z_7$ to $Z_{10}$ obtained by the foregoing method was packed in the fiber assembly as in Example 1 by the same manner and the same packing ratio as in Example 1 and they were united in a body as in Example 1. The extinction rate to Eumycetes was tested on each of the copper-zeolite powder-packed fiber articles thus obtained and the results are shown in Table 6. The method of measurement for the extinction rate of Eumycetes was conducted by the same manner as in Example 1. The sample marks of the copper-zeolite powder-packed fiber articles shown in Table 6 are as follows.

$F_7$: Fiber article packed with copper-A type zeolite powder ($Z_7$).

$F_8$: Fiber article packed with copper-Y type zeolite powder ($Z_8$).

$F_9$: Fiber article packed with copper-natural mordenite powder ($Z_9$).

$F_{10}$: Fiber article packed with copper-natural chabazite powder ($Z_{10}$).

TABLE 6

| | (Extinction rate to Eumycetes) | | | |
|---|---|---|---|---|
| Test fungus | $F_7$ | $F_8$ | $F_9$ | $F_{10}$ |
| *Aspergillus flavus* | 40% | 60% | 85% | 82% |

As is clear from Table 6, the copper-zeolite powder-packed fiber articles of this invention showed a considerably excellent bactericidal effect to *Aspergillus flavus* as shown by the values of the extinction rate.

COMPARISON EXAMPLE 2

Figure 3:
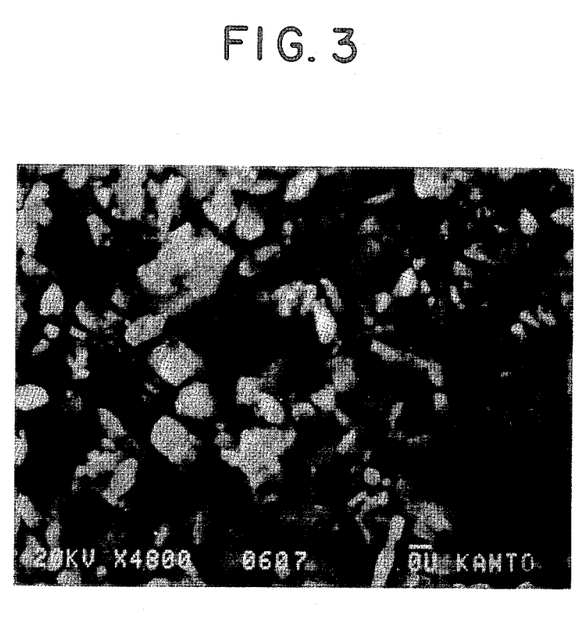
FIG. 3 is an electromicroscopic photograph of a copper-A-type zeolite converted by an undesired embodiment (Comparison example 2).

To 50 g of the A-type zeolite fine powder as used in Example 2 was added 200 ml of an aqueous 1M copper sulfate solution and the resultant mixture was stirred for 5 hours at room temperature. The copper-A type zeolite thus obtained was filtered by suction, washed with water until the sulfate ion disappeared, dried at 100°–105° C., and then pulverized to provide fine powder of the copper-A type zeolite. The converted copper-A type zeolite thus obtained contained $Cu_3(SO_4)(OH)_4$ as deposition thereof. The scanning electron microscopic photograph of the converted product thus obtained is shown in FIG. 3.

The converted copper-A type zeolite thus prepared was packed in a fiber assembly as in Example 1 and they were united in a body as in Example 1.

The extinction rate to Eumycetes by the copper-A type zeolite-packed fiber article was 20%.

EXAMPLE 3

To 1 kg of dry powder of A-type zeolite ($1.05Na_2O.Al_2O_3.1.92SiO_2.xH_2O$; water content 15.3%, fine powder finer than 100 mesh) was added 4 liters of an aqueous 2M zinc chloride solution and the resultant mixture was stirred for 3 hours and 20 minutes at 60° C. The zinc-zeolite thus obtained by such an ion exchange was separated by centrifugation. Thereafter, the foregoing batch process was repeated. In this example, the treatment by such a batch process was repeated four times. The zinc-zeolite finally obtained was washed with water to remove excessive zinc ion.

Then, the Zn-zeolite was dried at about 100° C. and pulverized to provide fine powder of the zinc-A type zeolite.

Also, to 200 g of each of two kinds of powder of natural zeolites, i.e., natural mordenite (2020A, trade name, made by Anaconda Minerals Company, fine powder finer than 100 mesh) and natural chabazite (5050L, trade name, made by Anaconda Minerals Company, fine powder finer than 100 mesh) was added 1 liter of an aqueous 1/20M zinc sulfate solution and the resultant mixture was stirred for 5 hours at room temperature to perform an ion exchange. The zinc-natural zeolite was filtered by suction and washed with water until the sulfate ion disappeared. Then, the washed zinc-natural zeolite was dried at 100°–105° C. and then pulverized to provide fine powder of zinc-natural zeolite.

The zinc content and the specific surface area of 3 kinds of the zinc-zeolites obtained in the foregoing methods are shown in Table 7.

TABLE 7

| Zeolite | Zinc content (%) of converted zinc-zeolite | Specific surface area (m²/g) of converted zinc-zeolite |
|---|---|---|
| A-type zeolite* | 23.5 | 435 |
| Natural mordenite* | 0.85 | 171 |
| Natural chabazite* | 1.25 | 463 |

*A-type zeolite: $1.05Na_2O.Al_2O_3.1.92 SiO_2.xH_2O$: fine powder finer than 100 mesh.
Natural Mordenite: 2020A, trade name, made by Anaconda Minerals Company, fine powder finer than 100 mesh.
Natural chabazite: 5050L, trade name, made by Anaconda Minerals Company, fine powder finer than 100 mesh.

(In the converted zinc-zeolites, the zinc-A type zeolite is abbreviated as $Z_{11}$, the zinc-natural mordenite as $Z_{12}$, and the zinc-natural chabazite as $Z_{13}$.)

Each of the converted zinc-zeolites $Z_{11}$ to $Z_{13}$ obtained by the foregoing methods was packed in a body in the fiber assembly as used in Example 1 by the same manner and packing ratio as those in Example 1. The test results for the extinction rate to Eumycetes by these zinc-zeolite powder-packed fiber articles are shown in Table 8. The extinction rate to Eumycetes was measured by the same manner as in Example 1. Also, the sample marks of the zinc-zeolite powder-packed fiber articles shown in Table 8 are as follows.

$F_{11}$: Fiber article packed with zinc-A type zeolite powder ($Z_{11}$).

$F_{12}$: Fiber article packed with zinc-natural mordenite powder ($Z_{12}$).

$F_{13}$: Fiber article packed with zinc-natural chabazite powder ($Z_{13}$).

TABLE 8

| | (Extinction rate to Eumycetes) | | |
|---|---|---|---|
| Eumycetes | $F_{11}$ | $F_{12}$ | $F_{13}$ |
| *Aspergillus flavus* | 90% | 82% | 80% |

As is clear from Table 8, the zinc-A type zeolite powder-packed fiber article showed sufficient bactericidal activity to *Aspergillus flavus*.

What is claimed is:

1. A particle-packed fiber article having an anti-bacterial property comprising zeolitic particles retaining therein at least one metal ion having a bactericidal property and having a specific surface area of at least 150 m²/g and a $SiO_2/Al_2O_3$ mol ratio of at most 14 and a mixed fiber assembly composed of a natural fiber staple or synthetic fiber staple and a fiber staple containing low-melting thermoplastic synthetic fibers having a melting point at least 30° C. lower than the melting point or the decomposition point of the aforesaid natural fiber staple or synthetic fiber staple, at least a part of the intersection points of the staple of said mixed fiber assembly being stuck to each other by the fusion of the low-melting thermoplastic synthetic fibers, whereby said zeolitic particles are incorporated and retained in the fiber assembly in the state of allowing the contact of the foregoing zeolitic particles with an external fluid.

2. The particle-packed fiber article having an antibacterial property as claimed in claim 1 wherein the zeolitic particles are composed of A-type zeolite, X-type zeolite, mordenite, or a mixture thereof.

3. The particle-packed fiber article having an antibacterial property as claimed in claim 1 wherein the zeolitic solid particles retain at least one metal ion having a bactericidal activity selected from the group consisting of silver, copper, and zinc at the ion-exchangeable sites thereof.

4. The particle-packed fiber article having an antibacterial property as claimed in claim 1 wherein the amount of the zeolite solid particles packed in the mixed fiber assembly is in a range of 0.1 to 60% by weight (as anhydrous zeolite) to the fiber.

* * * * *